United States Patent

Cheng et al.

[19]

[11] Patent Number: 6,028,664
[45] Date of Patent: Feb. 22, 2000

[54] METHOD AND SYSTEM FOR ESTABLISHING A COMMON REFERENCE POINT ON A SEMICONDUCTOR WAFER INSPECTED BY TWO OR MORE SCANNING MECHANISMS

[75] Inventors: Arnold Cheng, Chelmsford; Chin-Jung Hsu, North Andover; James Ni, Chelmsford, all of Mass.

[73] Assignee: Inspex, Inc., Billerica, Mass.

[21] Appl. No.: 08/833,217

[22] Filed: Apr. 14, 1997

Related U.S. Application Data

[63] Continuation-in-part of application No. 08/791,802, Jan. 29, 1997, abandoned.

[51] Int. Cl.[7] .............................. G01N 21/88; G06F 19/00
[52] U.S. Cl. ...................................... 356/237.4; 356/237.5; 364/468.28; 364/474.34; 382/149
[58] Field of Search ..................................... 356/237, 394, 356/375, 401; 364/468.16, 468.17, 468.28, 474.34, 474.35, 555.01; 382/145, 149, 151

[56] References Cited

U.S. PATENT DOCUMENTS

| 4,772,126 | 9/1988 | Allemand et al. . | |
|---|---|---|---|
| 5,086,477 | 2/1992 | Yu et al. ...................................... | 382/8 |
| 5,267,017 | 11/1993 | Uritsky et al. . | |
| 5,280,437 | 1/1994 | Corliss . | |
| 5,422,724 | 6/1995 | Kinney et al. . | |
| 5,539,752 | 7/1996 | Berezin et al. . | |
| 5,731,982 | 3/1998 | Namba et al. ..................... | 364/474.24 |

Primary Examiner—Robert H. Kim
Assistant Examiner—Zandra V. Smith
Attorney, Agent, or Firm—Kriegsman & Kriegsman

[57] ABSTRACT

A method and system for establishing a common reference point on a semiconductor wafer inspected by two or more scanning mechanisms. The semiconductor wafer includes a plurality of dies of identical size, each die being generally rectangularly shaped and having four corners. Adjacent dies are separated by a die street, the sum of the width of a die and the width of a die street equaling a die period. The method includes scanning the semiconductor wafer with a first scanning mechanism to establish a first coordinate system for the wafer. The first scanning mechanism determines a point on the wafer to be the center of the wafer which is assigned a first coordinate value relative to the first coordinate system. The location of the common reference point in the first coordinate system is calculated as the die corner which is within half the die period from the first coordinate value, the common reference point being assigned a second coordinate value in the first coordinate system. The semiconductor wafer is then scanned by a second scanning mechanism which establishes a second coordinate system for the wafer. The second coordinate value is located in the second coordinate system. The location of the common reference point in the second coordinate system can be calculated as the die corner which is within half the die period from the second coordinate value in the second coordinate system.

11 Claims, 4 Drawing Sheets

METHOD AND SYSTEM FOR ESTABLISHING A COMMON REFERENCE POINT ON A SEMICONDUCTOR WAFER INSPECTED BY TWO OR MORE SCANNING MECHANISMS

CROSS-REFERENCE TO RELATED APPLICATIONS

This application is a continuation-in-part of U.S. patent application Ser. No. 08/791,802 now abandoned, filed on Jan. 29, 1997 in the names of Arnold Cheng, Chin-Jung Hsu and James Ni.

BACKGROUND OF THE INVENTION

The present invention relates generally to the inspection of semiconductor integrated circuit (IC) chips and more particularly, to a method and system for establishing a common reference point on a semiconductor wafer inspected by two or more scanning mechanisms.

Integrated circuits (ICs) are commonly manufactured through a series of processing steps. Very often more than a hundred processing steps are performed to produce a properly functioning integrated circuit chip.

A semiconductor material, commonly in the shape of a wafer, serves as the substrate for integrated circuits. Semiconductor ICs are typically manufactured as an assembly of a hundred or more chips on a single semiconductor wafer, which is then cut up to produce the individual IC chips. Typically, a wafer made of silicon is used as the integrated circuit substrate, the silicon wafer being approximately 150–200 mm in diameter and 0.5–1 mm thick. During the manufacturing process, the silicon wafer is first polished and cleaned to remove all contaminant particles situated thereon. The silicon wafer is then treated in preparation for a series of processing steps involving a plurality of photolithographic patterns (also commonly referred to as masks). In the production of integrated circuits, microelectronic circuits are formed onto the silicon wafer through a process of layering. In the layering process, conductive and insulative layers of thin films are deposited and patterned onto the silicon wafer. Each layer is patterned by a mask designed specifically for it, the mask defining the areas within the wafer that are to be treated such as by etching or implanting.

Semiconductor fabrication technology today deals with silicon wafers which are approximately 200 mm in diameter and which feature geometries with dimensions well below 1 $\mu$m (micrometer). Due to the high complexity and level of integration of integrated circuits, the absence of contaminants on every layer of the wafer is critical in order to realize acceptable levels of product yield. Specifically, the presence of one contaminant particle larger than the half the width of a conductive line on the silicon wafer can result in complete failure of a semiconductor chip produced from the wafer. Such a wafer has to be discarded which thereby decreases the percentage yield per wafer and increases the overall cost of the individual chips. Therefore, a critical task facing semiconductor process engineers is to identify and, as far as possible, to eliminate sources of surface contamination on each layer of the semiconductor wafer.

Accordingly, inspection systems are well known in the art and are commonly used to detect and analyze the presence of contaminant particles on semiconductor wafers at a variety of positions along the production line of the integrated circuit. Commercially available patterned wafer inspection systems include system model numbers TPC 8500 and TPC 9000 manufactured by Inspex, Inc. of Billerica, Mass. Such inspection systems typically include one or more inspection instruments (such as laser scanning tools) which detect and locate particles on the wafer.

As example of an inspection instrument commonly used to detect particles on a semiconductor wafer, U.S. Pat. No. 4,772,126 to C. D. Allemand et al discloses an apparatus and method for detecting the presence of particles on the surface of an object such the front side of a patterned semiconductor wafer. A vertically expanded, horizontally scanning, beam of light is directed onto an area on the surface of the object at a grazing angle of incidence. A video camera positioned above the surface detects light scattered from any particles which may be present on the surface, but not specularly reflected light. The surface is angularly prepositioned (rotated) relative to the incident light beam so that the diffracted light from the surface and the pattern of lines on the surface is at a minimum. The object is then moved translationally to expose another are to the incident light beam so that the entire surface of the object or selected portions thereof can be examined, an area at a time. It is well known in the art for inspection systems to include a plurality of different inspection instruments, each inspection instrument being responsible for inspecting the wafer at a particle point in time during the manufacturing process. As such, each inspection instrument will inspect the semiconductor wafer after the treatment of a particular layer of the integrated circuit. By using multiple inspection instruments to scan various layers of the semiconductor wafer for contaminant particles, the user is able to discern where, and more specifically on which layer, a defect first occurred in the manufacturing process. The ability to discern where a defect first occurred is extremely useful in removing the defect and in preventing future contamination.

However, in order to detect where in the manufacturing process a defect first occurred, it is necessary to compare the location of the defects detected by each inspection instrument used to inspect a particular layer of the wafer. To effectively perform the comparison, all of the inspection instruments must have a common coordinate system. A common coordinate system for all the inspection instruments will ensure that if a defect is carried over to subsequent layers, the defect will have exactly the same coordinates in each layer. Otherwise, the user would be unable to determine whether a defect has been carried over from a previous layer or whether, in fact, the defect is new.

To establish a common coordinate system, it is well known in the art to select a common point on the semiconductor wafer as the origin of the wafer for each of the various inspection instruments. The point selected to be the origin for all the inspection instruments is generally given a coordinate value of (0,0) by which all other points are assigned a coordinate value in relation thereto.

It is well known in the art to use the center of the wafer as the origin to establish a common coordinate system for multiple inspection instruments, wherein each particle detected in each layer is denoted a coordinate value relative to the common reference point, the center of the wafer.

One drawback of such a system is that the point determined to be the center of the wafer may vary or drift from scanning tool to scanning tool. This condition is commonly referred to as center of the wafer (COW) drifting between inspection mechanisms. As a result of the center of the wafer drifting between inspection instruments, the coordinate values assigned by one inspection instrument for various points on the semiconductor wafer will not coincide with the coordinate values assigned by another inspection instrument for the same points. Since the same defects will be assigned different coordinate values by different scanning tools, the user will be precluded from effectively determining on which layer the particle was introduced to the wafer.

In U.S. Pat. No. 5,267,017 to Y. S. Uritsky et al there is disclosed a method for reducing targeting errors encountered when trying to locate contaminant particles in a high-magnification imaging device, based on estimates of the particle positions obtained from a scanning device. The method of the invention uses three techniques separately and in combination. The first technique includes selecting at least three reference particles, to provide multiple unique pairs of reference particles for computation of an averaged set of coordinate transformation parameters, used to transform particle position coordinates from the coordinate system of the scanning device to the coordinate system of the imaging device. The averaged transformation parameters result in much smaller targeting errors between estimated and actual positions of the particles. The targeting errors are further reduced by the use of multiple scans of the scanning device. In a third technique, accumulated reference particle targeting errors observed in prior processing of other wafers are used to reduce these targeting errors when processing a new wafer.

Other patents of interest include U.S. Pat. No. 5,539,752 to A. Berezin et al, U.S. Pat. No. 5,422,724 to P. D. Kinney et al, and U.S. Pat. No. 5,280,437 to D. A. Corliss.

SUMMARY OF THE INVENTION

It is an object of the present invention to provide a new and improved method and system for detecting contaminant particles on a semiconductor wafer during the manufacturing process of integrated circuit chips.

It is another object of the present invention to provide a method and system as described above which uses two or more inspection instruments to inspect the semiconductor wafer for contaminant particles.

It is yet another object of the present invention to provide a method and system as described above which establishes a common reference point on the semiconductor wafer for each of the inspection instruments used.

Accordingly, there is provided a method for establishing a common reference point on a semiconductor wafer inspected by two or more scanning mechanisms, said wafer having a plurality of dies of identical size, each die being generally rectangularly shaped and having four corners, adjacent dies being separated by a die street, the sum of the width of a die and the width of a die street equaling a die period, said method comprising the steps of scanning the semiconductor wafer with a first scanning mechanism, and selecting a die corner on said wafer as a common reference point for each of said scanning mechanisms.

There is also provided a data management system for establishing a common reference point on a semiconductor wafer inspected by two or more scanning mechanisms, the wafer including a plurality of dies of identical size, each die being generally rectangularly shaped and having four corners, adjacent dies being separated by a die street, the sum of the width of a die and the width of a die street equaling a die period, said data management system selecting a die corner as a common reference point on the wafer for all scanning mechanisms.

Various other features and advantages will appear from the description to follow. In the description, reference is made to the accompanying drawings which form a part thereof, and in which is shown by way of illustration, a specific embodiment for practicing the invention. The embodiment will be described in sufficient detail to enable those skilled in the art to practice the invention, and it is to be understood that other embodiments may be utilized and that structural changes may be made without departing from the scope of the invention. The following detailed description is therefore, not to be taken in a limiting sense, and the scope of the present invention is best defined by the appended claims.

BRIEF DESCRIPTION OF THE DRAWINGS

In the drawings wherein like reference numerals represent like parts.

DETAILED DESCRIPTION OF THE PREFERRED EMBODIMENT

Figure 1:
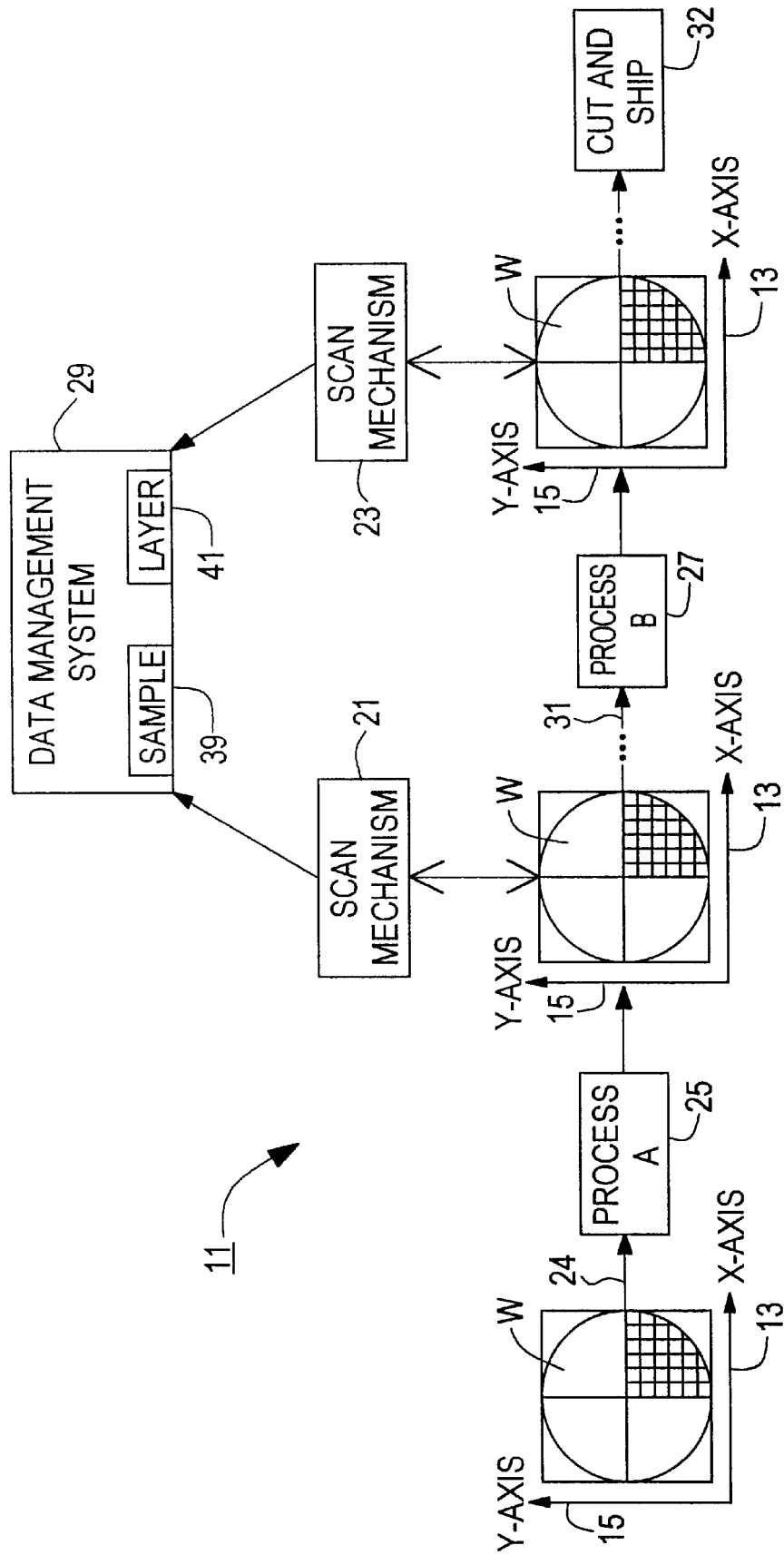
FIG. 1 is a partial block diagram of a sequence of operations performed on a silicon wafer during the manufacturing process of integrated circuits.

Integrated circuits are typically manufactured through a process in which multiple layers of thin films are deposited and patterned onto a wafer made of a semiconductor material, such as silicon. FIG. 1 shows a partial block diagram of a sequence of operations performed on a silicon wafer W during the manufacturing of a plurality of individual integrated circuits, the manufacturing process being identified generally by reference numeral 11.

Figure 2:
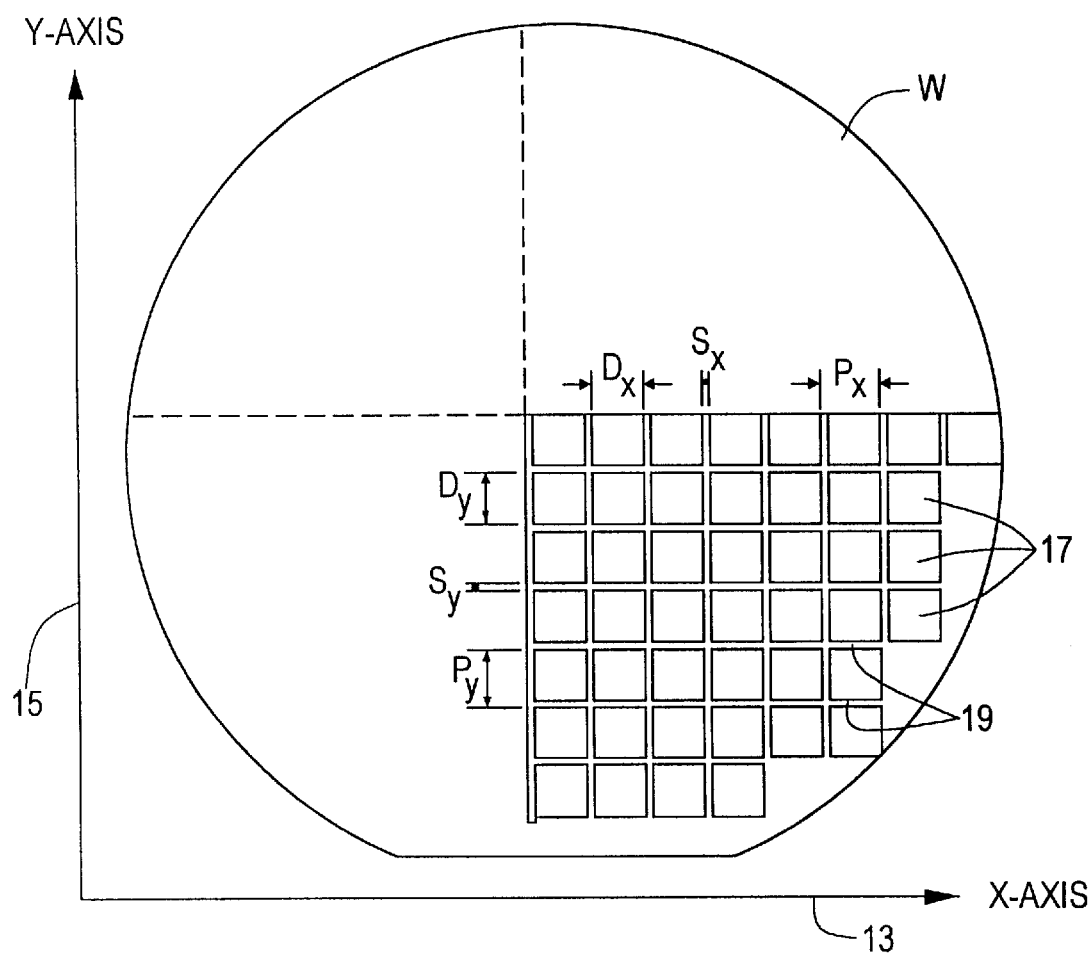
FIG. 2 is a top plan view of the silicon wafer at one point on the block diagram shown in FIG. 1, the wafer being shown relative to a Cartesian coordinate system having an X-axis and an orthogonal Y-axis.

FIG. 2 shows a top plan view of silicon wafer W shown relative to a Cartesian coordinate system having an X-axis 13 and an orthogonal Y-axis 15. Silicon wafer W comprises a plurality of wafer dies 17, each wafer die 17 serving as the basis for an individual IC chip upon the completion of manufacturing process 11. For simplicity, wafer dies 17 are only shown on one-quarter of wafer W. It should be noted that dies 17 are permanently etched on wafer W; therefore, throughout manufacturing process 11, the dimensions and relative position of each die 17 on wafer W remains constant as each layer is deposited and patterned.

Each die 17 on silicon wafer W is of identical size and dimension. Specifically, each wafer die 17 has a constant die width $D_x$ along X-axis 13 and a constant die width $D_y$ along Y-axis 15. Furthermore, adjacent dies are separated from one another by a die street 19 of identical size and dimension. Specifically, each die street 19 has a constant die street width $S_x$ along X-axis 13 and a constant die street width $S_y$ along Y-axis 15. The sum of the die width and the die street width is commonly referred to as the die period, which is calculated as shown below:

$D_x + S_x$ = Die period $P_x$ along X-axis 13

$D_y + S_y$ = Die period $P_y$ along Y-axis 15

The value of die periods $P_x$ and $P_y$ for each die 17 on wafer 11 are constant and are readibly calculable.

Due to the high complexity and level of integration of the integrated circuits produced on each die 17, the absence of contaminants on every layer of the semiconductor wafer is critical in order to realize acceptable levels of product yield. Accordingly, manufacturing process 11 comprises a pair of scanning mechanisms 21 and 23, also referred to as inspection tools, which are employed to identify surface contaminants on wafer W at particular points in time during manufacturing process 11.

As shown in FIG. 1, wafer W is started in manufacturing process 11 where indicated by line 24. At line 24, wafer W is preferably cleaned free of contaminants and has no layers deposited thereon (often referred to a virgin wafer at this stage) Process A is first performed on wafer 11 as indicated by block 25. Process step A represents any typical production step in the manufacturing of ICs, such as the deposition or patterning of a thin film onto wafer 11.

Figure 3:
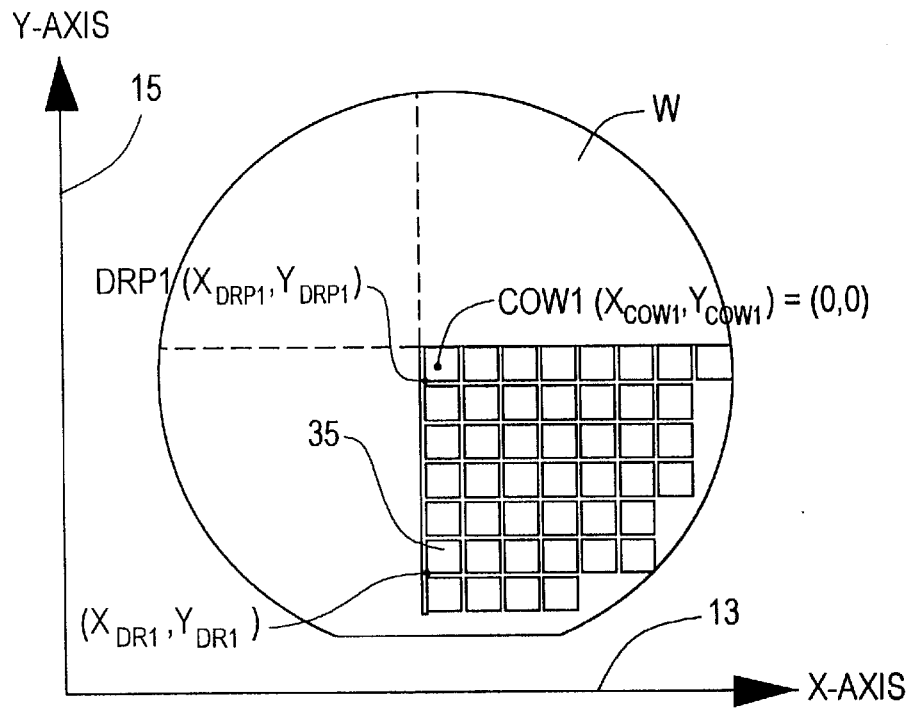
FIG. 3 is a top plan view of the silicon wafer another point on the block diagram shown in FIG. 1, the wafer being shown relative to a Cartesian coordinate system having an X-axis and an orthogonal Y-axis.

Following completion of Process A on wafer W, wafer scanning mechanism 21 is used to perform a visual inspection of wafer W. FIG. 3 shows a top plan view of wafer W at this point in manufacturing process 11. The results of the visual inspection performed by scanning mechanism 21 are sent to a data management system (DMS) which is represented by block 29. Data management system 29 serves to compile the results of the various scanning mechanisms used to inspect wafer W into an accessible central database.

Figure 4:
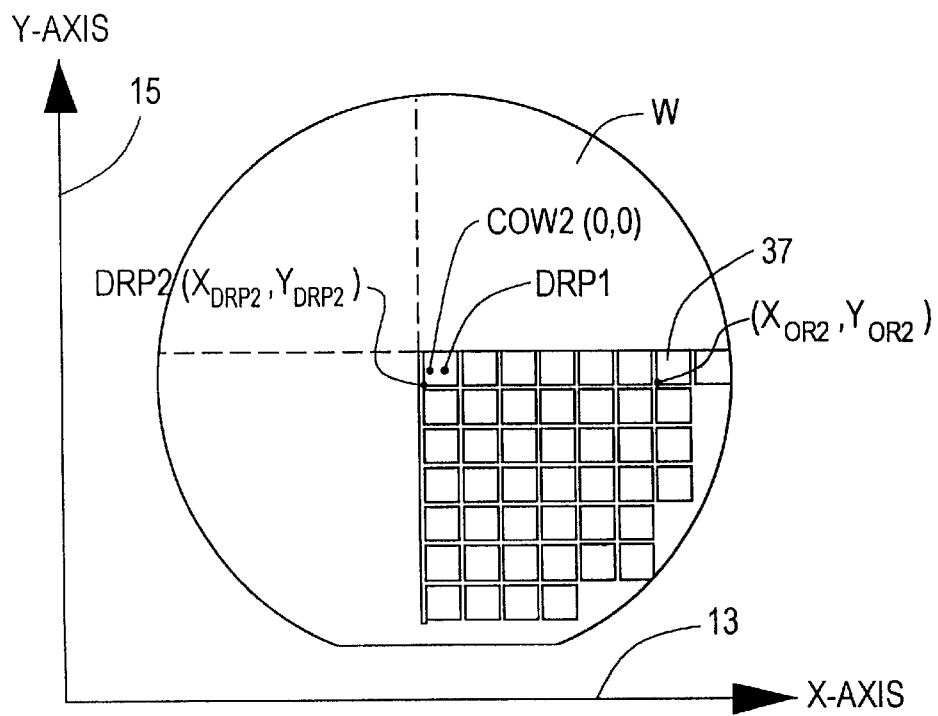
FIG. 4 is a top plan view of the silicon wafer another point on the block diagram shown in FIG. 1, the wafer being shown relative to a Cartesian coordinate system having an X-axis and an orthogonal Y-axis.

At line 31, process B is performed on wafer 11, process B being indicated by block 27. Upon completion of Process B in block 27, wafer scanning mechanism 23 is used to perform a visual inspection of wafer W. FIG. 4 shows a top plan view of wafer W at this point in manufacturing process 11. The results of the visual inspection performed by scan mechanism 23 are sent to data management system 29 for comparative analysis with the results compiled by scanning mechanism 21, as will described in detail below. After visual inspection by scan mechanism 23, wafer W is then cut and shipped as shown by box 32.

It should be noted, that manufacturing process 11 is not limited to two wafer treatment processes and two scanning mechanisms. Rather, manufacturing process 11 may include hundreds or thousands of treatment processes. Each process step, for example, comprises operations to be performed for a particular mask or layer of wafer W. Since the process steps are conventional and vary depending on the IC product being manufactured, they are not described in further detail and are limited to process steps A and B for simplicity. In addition, process 11 may comprise of additional scanning mechanisms to monitor wafer W for surface contaminants at other stages during manufacturing.

The visual inspection performed by scanning mechanisms 21 and 23 can be used to identify the coordinates of particular contaminants present on wafer W at different stages in process 11. The coordinates of the particular defects identified by mechanisms 21 and 23 are then analyzed by data management system 29. Data management system 29 tracks the locations of particular particles on wafer W detected by mechanisms 21 and 23 to determine where in manufacturing process 11 the particular particles were introduced. By determining where in process 11 a particular particle was introduced, and accordingly, the specific layer on which the particle is located, the user is better able to remove the contaminant as well as prevent future contamination in process 11, which is highly desirable.

In order to detect where in manufacturing process 11 a defect first occurred, data management system 29 must be able to effectively compare the location of the defects detected by each inspection tool. The location of the particular defects detected by each inspection tool is typically assigned a coordinate value relative to the point on the wafer which the inspection tool determines to be the center of the wafer (COW). The center of the wafer is generally assigned a coordinate value of (0,0) by which all other points on wafer W are determined relative thereto.

However, it has been found that very often different scanning mechanisms will select a different location on the wafer as its center of the wafer. This condition is commonly referred to as center of wafer (COW) drifting between multiple scanning instruments. As a consequence of COW drifting, each scanning mechanism will create a different coordinate system for the same wafer. The creation of different coordinate systems for the same wafer means that each scanning mechanisms will assign the same locations on wafer W different coordinate values, thereby precluding comparison between the mechanisms. To eliminate coordinate drifting, and to effectively integrate the various scanning mechanisms into a common coordinate system, it is necessary for all of the inspection instruments to locate a common reference point on wafer W by which all other points are assigned a coordinate value relative thereto. A common reference point, and accordingly a coordinate system, for all the inspection instruments will ensure that if a defect is carried over to subsequent layers, the defect will have exactly the same coordinates in each layer. Otherwise, the user would be unable to determine whether a defect has been carried over from a previous layer or whether, in fact, the defect is new.

Accordingly, data management system 29 includes a method for creating a common reference point among the multiple wafer scanning mechanisms, the method being provided by computer software in system 29. The method for creating a common reference point effectively enables the inspection results of scanning mechanisms 21 and 23 to be compared through the establishment of an integrated coordinate system.

In order to clearly describe the present method for establishing a common reference point, the method of the present invention is described in conjunction with process 11. However, it is to be noted that the present method is not limited to the number and type of processes and mechanisms shown in process 11.

The method for establishing a common reference point is as follows: Referring now to FIG. 3, scan mechanism 21 inspects wafer W and sends its results to data management system 29. As scanning mechanism 21 inspects wafer 21, mechanism 21 is disposed to assign a particular die on wafer W as its origin die 35. It should be noted that all inspection tools are disposed to select a particular die on a wafer as its origin die and that the origin die selected by the inspection tool on the wafer varies from scanning mechanism to scanning mechanism. As scanning mechanism 21 inspects wafer W, mechanism 21 is also disposed to attempt to locate the center of the wafer, the center of wafer being identified as COW1. It should be noted that all inspection tools are disposed to select a particular point on a wafer as its center of wafer and, as noted previously, the point on a wafer determined by the scanning mechanism to be the center of the wafer may vary from scanning mechanism to scanning mechanism (COW drifting). Once scanning mechanism 21 locates center of wafer COW1, all other points on wafer W are then assigned a coordinate value in relation to center of wafer COW1. For example, center of wafer COW1 will be assigned a coordinate value of (0,0), which is commonly referred to as the coordinate origin, by which all other points on wafer W are determined relative thereto. As a result, the lower left hand corner (LLHC) of origin die 35 is assigned a coordinate value in relation to center of wafer COW1, lower left hand corner of origin die 35 being identified by reference coordinates ($X_{OR1}$, $Y_{OR1}$). Because the die period is a known constant value, the location of the lower left hand corner of each die 17 in wafer W can be easily calculated in relation to lower left hand corner $X_{OR1}$, $Y_{OR1}$ of origin die 35 by adding a multiple of $P_x$ and $P_y$ thereto.

Data management system 29 then determines whether scanning mechanism 21 is the first mechanism used to inspect wafer W by searching within a SAMPLE DRP table 39 in data management system 29 to see if there is data stored in its memory for the particular wafer. Because scanning mechanism 21 is the first scanning mechanism used to inspect wafer W, there is no data stored within SAMPLE DRP table 39. Data management system 29 then locates the die in which its lower left hand corner is within half the die period of center of wafer COW1. The lower left hand corner located serves as the common data reference point on wafer W for all scanning mechanisms used to inspect wafer W in process 11.

It should be briefly noted that although the lower left hand corner is used as the common data reference point throughout process 11, the present invention is not limited to the selection of the lower left hand corner as the reference point. Rather, either of the four die corners could be selected and used in the manner to be described below.

For scanning mechanism 21, the data reference point is identified as DRP1 and has the coordinate values $X_{DRP1}$, $Y_{DRP1}$. Data management system 29 calculates the exact location of DRP1 by adjusting lower left hand corner $X_{OR1}$, $Y_{OR1}$ of origin die 35 by one die period at a time towards center of wafer COW1 until its distance from center of wafer is within half the die period $P_x$, $P_y$. This calculation to determine data reference point DRP1 can be easily accomplished by using a basic computer program such as the one set forth below (in the program the origin die defined by the scanning tool refers to the lower left hand corner of the origin die and the reference point refers to the center of the wafer):

```
x_period = x_die_size + x_die_street;
y_period = y_die_size + y_die_street;
void calculate_drp (double x_origin, double y_origin,
      double x_period, double y_period,
      double x_ref, double y_ref,
      double *x_drp, double *y_drp)
{
  double l;
  double x,y;
  /*
  **Initialize
  */
  x = x_origin;      /* Origin Die defined by scanning tool */
  y = y_origin;
  x = x - x_ref;     /* Origin Die relative to reference point */
  y = y - y_ref;
  /*
  **Calculate X_DRP
  */
  l = x_period/2;    /* half of x die period */
  if (x >= 0)        /* adjust one period at a time toward reference
                        point */
```

```
    for(; x >= l;)
        x = x - x_period;
    else
        for(; x <- l;)
            x = x + x_period;
    /*
    **Calculate Y_DRP
    */
    l = y_period/2;    /* half of y die period */
    if (y >= 0)        /* adjust one period at a time toward reference
                          point */
        for(; y >= l;)
            y = y - y_period;
    else
        for(; y <- l;)
            y = y + y_period;
    *x_drp = x + x_ref;    /* Result - DRP location, relative to
                              the origin (0,0) defined by the tool */
    *y_drp = y + y_ref;
}
```

Having determined the exact coordinates of data reference point DRP1 relative to center of wafer COW1 (center of wafer COW1 serving as the origin (0,0) defined by mechanism 21), coordinate values $X_{DRP1}$, $Y_{DRP1}$ are recorded into SAMPLE DRP table 39 in data management system 29 for future use for other scanning mechanisms used to inspect wafer W. Coordinate values $X_{DRP1}$, $Y_{DRP1}$ are additionally updated in a LAYER DRP table 41 in data management system 29, LAYER DRP table 41 serving as a compilation of the coordinate values of the common reference point determined by each scanning tool used to inspect wafer W.

Referring now to FIG. 4, as scan mechanism 23 inspects wafer W, mechanism 23 is disposed to assign a particular die on wafer W as an origin die 37. As scanning mechanism 23 inspects wafer W, mechanism 23 is also disposed to attempt to locate the center of the wafer, the center of wafer being identified as COW2. Once scanning mechanism 23 locates center of wafer COW2, all other points on wafer W are then assigned a coordinate value in relation to center of wafer COW2. Typically, center of wafer COW2 will be assigned a coordinate value of (0,0) by which all other points on wafer W are determined relative thereto. The lower left hand corner (LLHC) of origin die 37 is assigned a coordinate value in relation to center of wafer COW2, lower left hand corner of origin die 37 being identified by reference coordinates ($X_{OR2}$, $Y_{OR2}$). Because the die period is a known constant value, the location of the lower left hand corner of each die 17 in wafer W can then be easily calculated in relation to lower left hand corner $X_{OR2}$, $Y_{OR2}$ of origin die 37.

Data management system 29 then determines whether scanning mechanism 23 is the first mechanism used to inspect wafer W by searching within SAMPLE DRP table 39 to see if there is data stored in its memory for this particular wafer W. Because a data reference point already exists in the SAMPLE DRP table from mechanism 21, defect analysis system 29, as well as all future inspection tools used to scan wafer W, calculates a data reference point DRP2 for scan mechanism 23 in relation to data reference point DRP1 located in the SAMPLE DRP table.

Specifically, for scan mechanism 23, data management system 29 locates the die of wafer W in which its lower left hand corner is within a distance of half the die period from data reference point DRP1 ($X_{DRP1}$, $Y_{DRP1}$). The data reference point calculated for scanning mechanism 23 is identified as DRP2 and has the coordinate values $X_{DRP2}$, $Y_{DRP2}$.

Data management system 29 determines the exact location of data reference point DRP2 by adjusting lower left hand corner $X_{OR2}$, $Y_{OR2}$ of origin die 37 by one die period at a time towards data reference point DRP1 until it is within half die period $P_x$, $P_y$ of data reference point DRP1. The calculation of data reference point DRP2 can be easily accomplished by using the computer program set forth above, except with the reference point being data reference point DRP1 ($X_{DRP1}$, $Y_{DRP1}$) rather than the center of wafer COW.

Having determined the exact coordinates of second data reference point DRP2 relative to the center of wafer COW2, coordinate values $X_{DRP2}$, $Y_{DRP2}$ are recorded in LAYER DRP table 41. Additional inspection tools would accordingly update its coordinate values for the common data reference point in a similar manner as described in conjunction with mechanism 23 such that LAYER DRP table 41 would compile the coordinates of the common reference point for each scanning tool used to inspect wafer W.

Since LAYER DRP table 41 includes the coordinates of the common data reference point on wafer W for each instrument used, data management system 29 can then normalize the common data reference point for each scanning mechanism as the origin point (0,0) by which all other points are determined in relation thereto. This creates a common coordinate system for all scanning instruments used to inspect wafer W, as is desired. The normalization of the common data reference point for all of the scanning mechanisms could be accomplished by using a simple software program.

Figure 5:
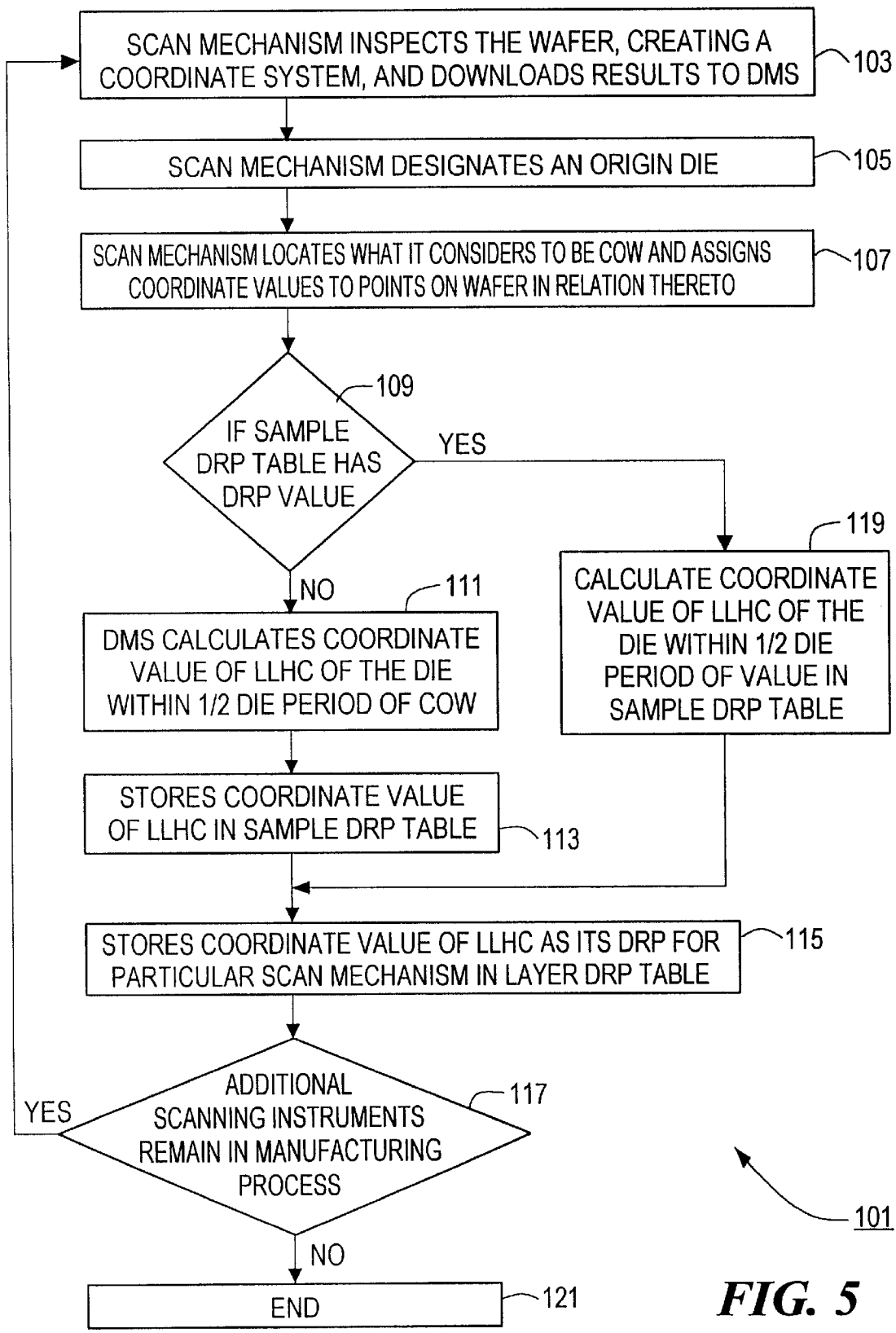
FIG. 5 is a flow diagram of the method of the present invention for establishing a common reference point on the wafer inspected by two or more scanning mechanisms.

To further understand the present invention, a brief numerical example will be described below in conjunction with the method of the present invention for establishing a common reference point on a semiconductor wafer inspected by two or more scanning tools. FIG. 5 shows a flow chart displaying the method for establishing a common reference point, the method being represented by reference numeral 101. Assume that wafer W has a constant, known die period of:

$P_x$=100 and $P_y$=100.

In step 103, the first scanning mechanism inspects the wafer and downloads its results to data management system 29. In steps 105 and 107, assume that scan mechanism 21 assigns the lower left hand corner of origin die 35 the following coordinates relative to center of wafer COW1 (0,0):

$X_{OR1}$=960 and $Y_{OR1}$=1560

Data management system 29 then determines whether there are DRP values in SAMPLE DRP table 39, as shown in step 109. Because it does not, system 29 then determines the DRP using step 111.

Step 111 requires system 29 to calculate the data reference point by adjusting $X_{OR1}$, $Y_{OR1}$ one period at a time toward center of wafer COW1 (0,0) until it is within half the die period. Accordingly:

$X_{OR1}$=960 is adjusted to center of wafer COW1 one period at a time. Specifically, 960 is subtracted by 100 until it is within half the die period, $P_x/2=100/2=50$.
So, 960−100=860; 860−100=760 . . . 60−100=−40, which is now within half the die period of 50 from center of wafer COW1 (0,0). Similarly, $Y_{OR1}$=1560 is adjusted to center of wafer COW1 one period at a time. Specifically, 1560 is subtracted by 100 until it is within half the die period, $P_y/2=100/2=50$.
So, 1560−100=1460; 1460−100=1360 . . . 60−100=−40, which is now within half the die period of 50 from center of wafer COW1 (0,0).

Therefore, data reference point DRP1 has the coordinate value of (−40, −40).

Next, as shown in step 113, the coordinate value of data reference point DRP1 is stored in SAMPLE DRP table 39. Additionally, the coordinate value of data reference point DRP1 is stored in LAYER DRP table 41 for that particular scanning tool, as shown in step 115.

As shown in step 117, because there is an additional scanning mechanism used in process 11, the scanning tool 23 repeats steps 103–109. Assume that scan mechanism 23 assigns the lower left hand corner of origin die 37 the following coordinates relative to center of wafer COW2 (0,0):

$X_{OR2}$=−550 and $Y_{OR2}$=−750

Because SAMPLE DRP table 39 has a stored value, as shown in step 119, the data reference point for the second inspection tool is calculated by adjusting $X_{OR2}$, $Y_{OR2}$ one period at a time toward data reference point DRP1 (−40,−40) until it is within half the die period, as shown by step 119. Accordingly:

$X_{OR2}$=−550 is adjusted to data reference point DRP1 (−40,−40) one period at a time. Specifically, −550 is added by 100 until it is within half the die period, $P_x/2=100/2=50$ of DRP1 (−40,−40).
So, −550+100=−450; 450+100=−350 . . . 150+100=−50, which is now within half the die period (50) from DRP1 ($X_{DRP1}$−40). Similarly, $Y_{OR2}$=−750 is adjusted to data reference point DRP1 one period at a time. Specifically, −750 is added by 100 until it is within half the die period, $P_y/2=100/2=50$.
So, −750+100=−650; 650+100=−550 . . . 150+100=−50, which is now within half the die period (50) from DRP1 ($Y_{DRP1}$=−40).

Therefore, data reference point DRP2 has the coordinate value of (−50, −50). This value is similarly stored in LAYER DRP table 41 for the second inspection tool, as shown in step 115. This means the exact same point on wafer W is assigned a coordinate value of (−40,−40) by scan mechanism 21 and a coordinate value of (−50,−50) by scan mechanism 23.

As shown in step 117, because there are no further scanning tools used in process 11, method 101 is finished as shown in step 121. At this time, a simple computer program can be implemented in data management system 29 to normalize make as coordinate origin point (0,0)) the data reference points in LAYER DRP table 41 to create a common coordinate system.

It should be known that different scanning mechanisms define the lower left hand corner of a die differently. For example, one tool may use the center of the cross of die streets as the lower left hand corner of the die and another tool may use the edge of the cross of die streets as the lower left hand corner of the die. The offsets of the different lower left hand corners selected by the various inspection tools are determined relative to a particular lower left hand corner chosen to be the standard. The offsets are then stored in the LAYER DRP table and should be used for compensation in the calculation of the data reference point DRP such as by using a computer program such as set forth below:

if (x_offset !=0 or y_offset !=0){
x_drp=x_drp−x_offset;
y_drp=y_drp−y_offset;

It is also important to note that the validity of the above-described method is contingent on the fact that the center of wafer (COW) drifting between two or more scanning mechanisms on a wafer is always less than half the die period.

The embodiments shown of the present invention are intended to be merely exemplary and those skilled in the art shall be able to make numerous variations and modifications to it without departing from the spirit of the present invention. All such variations and modifications are intended to be within the scope of the present invention as defined in the appended claims.

What is claimed is:

1. A method for establishing a common reference point on a semiconductor wafer inspected by two or more scanning mechanisms, said wafer having a plurality of dies of identical size, each die being generally rectangularly shaped and having four corners, adjacent dies being separated by a die street, the sum of the width of a die and the width of a die street equaling a die period, said method comprising the steps of:

(a). scanning the semiconductor wafer with a first scanning mechanism, and (b). selecting a die corner on said wafer to be a common reference point for each of said scanning mechanisms.

2. The method as defined in claim 1 wherein the lower left hand corner of a die on said wafer is selected as the common reference point for each of said scanning mechanisms.

3. A method for establishing a common reference point on a semiconductor wafer inspected by two or more scanning mechanisms, said wafer having a plurality of dies of identical size, each die being generally rectangularly shaped and having four corners, adjacent dies being separated by a die street, the sum of the width of a die and the width of a die street equaling a die period, said method comprising the steps of:

(a). scanning the semiconductor wafer with a first scanning mechanism, said first scanning mechanism establishing a first coordinate system for said wafer, said first scanning mechanism determining a point on the wafer to be the center of the wafer, the center of the wafer being assigned a first coordinate value in said first coordinate system, and (b). calculating the location of a common reference point in said first coordinate system, said common reference point being the die corner which is within half the die period from the first coordinate value, said common reference point being assigned a second coordinate value in said first coordinate system.

4. The method as defined in claim 3 wherein the calculation of the location of said common reference point in said first coordinate system is implemented by a computer program.

5. The method as defined in claim 3, and further comprising the steps of:

scanning the semiconductor wafer with a second scanning mechanism, said second scanning mechanism establishing a second coordinate system for said wafer, locating the second coordinate value in said second coordinate system, and calculating the location of said common reference point in second coordinate system, said common reference point being the die corner which is within half the die period from the second coordinate value in said second coordinate system, said common reference point being assigned a third coordinate value in said second coordinate system.

6. The method as defined in claim 5 wherein the calculation of the location of said common reference point in said second coordinate system is implemented by a computer program.

7. A data management system for establishing a common reference point on a semiconductor wafer inspected by two or more scanning mechanisms, the wafer including a plurality of dies of identical size, each die being generally rectangularly shaped and having four corners, adjacent dies being separated by a die street, the sum of the width of a die and the width of a die street equaling a die period, wherein said data management system selects a die corner to be a common reference point on the wafer for all scanning mechanisms.

8. The data management system as defined in claim 7 wherein said data management system selects the lower left hand corner of a die as said common reference point on the wafer for all scanning mechanisms.

9. The data management system as defined in claim 8 wherein said system calculates the location of said common reference point relative to the coordinate system established by each scanning mechanism.

10. The data management system as defined in claim 9 wherein said system calculates the location of said common reference point relative to the coordinate system established by each scanning mechanism by a computer program.

11. The data management system as defined in claim 10 wherein said system includes a storage table, the location of said common reference point relative to the coordinate system established by each scanning mechanism being retrievably stored in said storage table.

* * * * *